(12) United States Patent
Rhee et al.

(10) Patent No.: US 8,758,262 B2
(45) Date of Patent: Jun. 24, 2014

(54) RESPIRATORY DISEASE MONITORING SYSTEM

(75) Inventors: Hyekyun Rhee, Pittsford, NY (US);
Mark Bocko, Caledonia, NY (US)

(73) Assignee: University of Rochester, Rochester, NY (US)

( * ) Notice: Subject to any disclaimer, the term of this patent is extended or adjusted under 35 U.S.C. 154(b) by 626 days.

(21) Appl. No.: 12/954,440

(22) Filed: Nov. 24, 2010

(65) Prior Publication Data

US 2011/0125044 A1 May 26, 2011

Related U.S. Application Data

(60) Provisional application No. 61/264,539, filed on Nov. 25, 2009.

(51) Int. Cl.
*A61B 5/08* (2006.01)
(52) U.S. Cl.
USPC .......................................... 600/534; 600/529
(58) Field of Classification Search
CPC ................................ A61B 7/003; A61B 5/113
USPC .................................................. 600/529–543
See application file for complete search history.

(56) References Cited

U.S. PATENT DOCUMENTS

| 2004/0236241 | A1* | 11/2004 | Murphy ........................ | 600/529 |
| 2005/0080461 | A1* | 4/2005 | Stahmann et al. .............. | 607/17 |
| 2009/0191521 | A1* | 7/2009 | Paul et al. ...................... | 434/169 |
| 2012/0190949 | A1* | 7/2012 | McCombie et al. ........... | 600/324 |
| 2012/0245439 | A1* | 9/2012 | Andre et al. ................... | 600/529 |

OTHER PUBLICATIONS

Knocikova, et al., "Wavelet Analysis of Voluntary Cough Sound in Patients With Respiratory Diseases" J. of Physiology and Pharmacology, 2008, 331-340, vol. 59 Supple. 6.
Levy, et al., "Wheeze Detection: Recordings vs, Assessment of Physician and Parent" J. of Asthma, 2004, 845-853, vol. 41 No. 8.
Taplidou, et al., "Wheeze detection based on time-frequency analysis of breath sounds" Computers in Biology and Medicine, 2007, 1073-1083, vol. 37.
Matos, et al., " an Automated System for 24-h Monitoring of Cough Frequency: The Leicester Cough Monitor" IEEE, 2007, 1472-1478, vol. 54 No. 8.
Barry, et al., "The automatic recognition and counting of cough" Cough, 2006, 1-9, vol. 2 No. 8.
Murata, et al., "New Non-invasive Automatic Cough Counting Program Based on 6 Types of Classified Cough Sounds" Internal Medicine, 2006, 391-397, vol. 45 No. 6.

* cited by examiner

*Primary Examiner* — Michael Kahelin
*Assistant Examiner* — Karen Toth
(74) *Attorney, Agent, or Firm* — James W. Hill; McDermott Will & Emery LLP

(57) ABSTRACT

An automated system for monitoring respiratory diseases, such as asthma, provides noninvasive, multimodal monitoring of respiratory signs and symptoms that can include wheeze and cough. Some embodiments employ a mobile device, such as a cell phone, in which raw data from a microphone and an accelerometer are processed, analyzed, and stored. Data can be collected continuously. Time domain and frequency domain analyses of signals to determine, e.g., energy, duration, and spectral content of candidate sounds can be employed to discriminate symptoms of interest from background sounds and to establish significance. Accelerometer signals are analyzed to determine activity levels. Analyses of a user's symptoms and activity level prior to, during, and after an event can provide meaningful determinations of disease severity and predict future respiratory events. The system can provide a summary of data, as well as an alarm when symptom severity reaches a threshold.

20 Claims, 7 Drawing Sheets

RESPIRATORY DISEASE MONITORING SYSTEM

RELATED APPLICATIONS

This application claim priority benefit under 35 U.S.C. §119(e) of U.S. Provisional Application No. 61/264,539, filed Nov. 25, 2009, the entire contents of which are incorporated herein by reference.

STATEMENT REGARDING FEDERALLY SPONSORED RESEARCH OR DEVELOPMENT

This invention was made with government support under Grant 1R01 NR011169-01A1, dated Sep. 29, 2009, awarded by the National Institutes of Health/National Institute of Nursing Research. The government has certain rights in the invention.

FIELD OF THE INVENTIONS

Embodiments are described that relate to medical diagnostic equipment, particularly equipment for use by outpatients to monitor respiratory diseases such as asthma.

BACKGROUND

Asthma represents a serious health problem in the United States (U.S.) despite recent advances in treatment options. According to the national data collected from 2001-2003, the average prevalence of current asthma in the U.S. population was over 7%, and the rates of asthma attacks during the preceding 12 months in those with current asthma ranged from 53% to 56%. Thus, *Healthy People* 2010 recognized asthma as one of its target health problems and has established specific goals including reducing asthma deaths, hospitalization related to asthma, emergency department visits for asthma exacerbations, activity limitations and missed school days related to asthma episodes.

Although asthma affects people of all ages, children and adolescents are disproportionately affected by the disease compared to other age groups. In fact, asthma is the most common chronic disorder in childhood. The prevalence of asthma in U.S. children and adolescents has increased steadily over the past two decades although the trend has plateaued in recent years. In 2006, based on CDC data, an estimated 6.8 million children under the age of 18 were affected, of which 4.1 million suffered from an asthma attack or episode. National surveillance data of 2001-2003, the most recent period for which data are available, revealed that asthma in children and adolescents annually accounted for 4.7 million physician visits, nearly 700,000 emergency department visits, and over 200,000 hospitalizations. Estimated annual health care costs for treating asthma in children in the U.S. are approximately $14.7 billion, and indirect costs (e.g. lost productivity by adult caretakers) add another $5 billion, for a total of $19.7 billion. Pediatric asthma, the leading cause of school absenteeism, is responsible for 12.8 million missed school days in the U.S. annually, and 24% of children with asthma report asthma-related activity limitations. Asthma also affects children's perception of their general health. While the majority of children (98%) under age 17 in the U.S. reported that they were in good to excellent health, only 4% of children with asthma reported a comparable degree of health.

Contrary to the common belief that asthma severity and morbidity is less in adolescents than in children, asthma remains a serious problem for many adolescents into adulthood. According to a recent CDC report, over 15% of high school students reported current asthma, of whom 40% had experienced asthma attacks or episodes during the preceding 12 months. In fact, asthma attacks are as common for adolescents as for younger children. Near-fatal episodes are highest among those 12-15 years of age. Severe exacerbations requiring hospitalization, intubations and cardiopulmonary resuscitation are more common in adolescents than in younger children. Despite high asthma morbidity, adolescents are less likely to use health care services than younger children.

A desire to overcome the emotional burdens and to gain peer approval through conforming to peers can make adolescents with asthma more vulnerable to risk behaviors. Anxiety and depressive disorders are associated with increased risk for smoking in adolescents with asthma. Adolescents with asthma tend to have more positive attitudes toward smoking, show a stronger intention to become smokers, and to have a self-image more closely linked to smoking than their non-asthmatic peers. Despite known risks, adolescents with asthma are more likely to smoke or at least as likely as their healthy counterparts to smoke. In large population-based studies in the U.S., 56% of adolescents with asthma reported lifetime smoking (ever smoked) and 20% to 30% engaged in current smoking. A study noted that adolescents who failed to take their asthma medication, despite asthma symptoms, smoked nearly twice as much as those who adhered to asthma treatment. Given its substantial and devastating impact at the individual, family and socioeconomic levels, strategies to assist adolescents in efficient asthma monitoring and management are imperative.

SUMMARY OF THE INVENTIONS

Although much of the discussion herein focuses on asthma, this is meant only by way of example. Embodiments of the disclosure are also suitable for monitoring all sorts of both obstructive and restrictive lung diseases, both acute and chronic, such as emphysema, chronic obstructive pulmonary disease, pulmonary fibrosis, sarcoidosis, and many others.

Adolescence is a time of transformation that is accompanied by dramatic growth and changes in biological, emotional, cognitive and social domains. Adolescents with asthma deal with the same developmental demands as their healthier peers such as body image, identity, peer acceptance, emotional and financial independence and emerging sexuality. Chronic health conditions can complicate adolescents' journey into adulthood through physical and social limitations and challenges, and require young people to adjust to changes from normative patterns of development. Sense of self and identity may be threatened in these adolescents when they perceive themselves to be different from their peers because of the visible nature of symptoms and management protocol (e.g., use of inhaler or peak flow monitoring) and limitations in physical activity. These challenges can impact adolescents' personal and social identities, ultimately affecting how they choose to live and manage their illness. Conflicts between demands of the illness and developmental needs often place adolescents at risk for worsening asthma morbidity primarily related to poor self-management.

In spite of the challenges and issues, adolescence presents a unique opportunity for an intervention to improve asthma control. Adolescents are cognitively capable of grasping complex mechanisms involving pathophysiology of asthma and its management including prevention and treatments. Thus, they are capable and motivated to learn these skills, and knowledge and skills mastered in this period can last through adulthood. In addition, with a growing desire for independence and autonomy, adolescents want to take ownership in managing their illness. Parental influence on asthma care in their children dwindles as adolescents gradually assume primary responsibility for managing their own asthma. Adolescents believe that self-managed asthma is preferable to management by parents and often take responsibility for their asthma care whether they are ready or not.

The momentum presented by cognitive and psychosocial development is often offset by other developmental characteristics in adolescence. In some cases, adolescents' cognitive development may not be sufficient to process information related to their treatment regimens. Studies have suggested that adolescents' cognitive difficulties in remembering, understanding and following treatment regimens may interfere with adequate self-management. Specifically, "forgetting" is one of the most common barriers in adolescents. Adolescents' everyday life becomes increasingly complex with extended roles and social activities. Assuming daily asthma care may compete with other activities on which adolescents place priority; thus taking care of asthma becomes easily forgotten or neglected. Furthermore, adolescents' personal beliefs of invulnerability along with the desire to maintain normalcy interfere with their capacity to make responsible decisions, leaving them less proactive in managing asthma. In line with their invulnerability belief and aspiration to be normal, adolescents are often unwilling to comply with medical advice or purposefully disregard or downplay their symptoms. Denial is also not uncommon in adolescents. Many adolescents deny the fact that they have asthma or falsely believe that their nonadherence would not result in serious outcomes. Adolescents' tendency to focus on immediate consequences further threatens effective long-term prevention of asthma complications. Therefore, it can be difficult to convince an adolescent to take long-term controller medications and to carefully monitor symptoms on a regular basis. Negative attitudes toward asthma are widespread in adolescents. The negative attitudes reflected in poor relationships with health care providers, low treatment expectations, and perceiving asthma as unpredictable and uncontrollable, are powerful predictors of inadequate adherence to management regimens in children and adolescents.

The social milieu and peer dynamics often dictates adolescents' emotions and behaviors as they strive to achieve a sense of normalcy and/or conformity through peer approval. One study reported that only 39% of adolescents with asthma had disclosed their asthma to their friends, and 29% felt embarrassed about having an asthma attack in front of their friends. Adolescents who experience embarrassment about their asthma in the presence of peers are reluctant to take their asthma medication in the presence of their friends. Another recent study reported peer influence as one of the barriers to self-management in adolescents. Asthma-related circumstances (e.g., activity limitations, treatments) that impinge on the sense of normalcy and desired peer interactions ultimately take a toll on adolescents' emotional functioning. Therefore, it is not surprising that psychological difficulties (e.g., anxiety, depression, withdrawal, isolation, low self-esteem, decreased confidence as well as feelings of inadequacy, and helplessness) are common in adolescents with asthma.

Specific developmental challenges germane to adolescence call for an exclusive focus on this developmental stage for studies that intend to influence health outcomes in asthma. Asthma management in adolescents is challenged by dismissive attitudes toward their illness and symptoms that cause them to be less vigilant in monitoring changes in their asthma conditions, placing them at risk for negative health consequences by failing to assume timely and necessary self-management actions (e.g., taking medications, avoiding triggers, communicating with clinicians). Reinforcing sustainable and reliable symptom monitoring routines is of significant importance in ascertaining optimum asthma care, thus it is advantageous to offer adolescents an alternative symptom-monitoring strategy that excites their motivation for long-term adherence while minimizing compromise of their desire for normalcy.

Asthma-related morbidity in adolescents can be largely prevented by effective self-management. Self-management requires active commitment to engage in care processes by establishing individual routines including symptom monitoring, trigger avoidance and adherence to medication plans. Successful asthma management begins with the patient's accurate assessment of asthma symptoms. Symptom monitoring informs patient decisions to initiate appropriate self-management behaviors (e.g., adjusting medication, altering activity level, altering the surrounding environment or seeking medical assistance) as well as providers' decisions related to an appropriate treatment course. A recent Cochrane review revealed that appropriate symptom monitoring in children and adolescents can lead to fewer cases of asthma exacerbation and acute care visits for asthma as well as better functional outcomes and higher quality of life. Greater accuracy of symptom perception is associated with less school absenteeism and fewer emergency department visits even after controlling for underlying asthma severity.

Having recognized the importance of symptom monitoring in effective asthma management, current guidelines give a primary focus on the importance of ongoing patient-initiated symptom-based monitoring or peak expiratory flow (PEF) monitoring.

Symptom-based monitoring is the easiest method of asthma management, but many researchers have concurred that symptom reports by both children and parents are often inaccurate. Inaccurate symptom-based monitoring is considered a major threat to optimum asthma management. Symptom perception refers to the conscious awareness of a symptom, which is based on unconscious information processing. It has been reported that there is a higher degree of perceptual inaccuracy in children and parents during what they thought were asymptomatic (stable) periods than during symptomatic (unstable) periods. Asthma symptom perception may be inaccurate or biased by either blunted perception (underperception) or overperception. Blunted perception may result in denial, delay in seeking help and suboptimal treatment while overperception leads to unwarranted activity restrictions, high risk for adverse effects caused by overuse of medication and overutilization of health care resources. In the literature, blunted perception appears more common in children and adolescents than overperception. Underperception in young people is often suspected when the extent of reported limitations of daily activities is disproportionately greater than reported asthma symptoms. Adolescents exhibit predominately a tendency for underperception. Several factors contribute to inadequate symptom perception in children and adolescents, including the chronic nature of asthma, nocturnal symptoms, and high asthma severity.

The chronic nature of asthma is an important factor influencing underestimation of symptoms by children and adolescents. It has been found that adolescents with a longer duration of asthma were more likely to be represented in the inaccurate groups characterized by underperception. Children and adolescents become habituated and adapted to prolonged symptoms which may reduce the accuracy of symptom perception and lead to indifference to symptoms or neglect. As children become habituated, asthma episodes are less likely to accompany negative emotions, which may reduce perceptual accuracy. In the face of chronicity of the illness, parents and family members may also become adapted and less sensitive to subtle changes in asthma conditions or downplay legitimate asthma symptoms in children; thus delaying or omitting adequate and timely treatment actions. One researcher suggested that ineffective or inappropriate family response to asthma symptoms can impair children's ability to accurately perceive their symptoms.

Underrated asthma symptoms also may be a result of patients' inability to recount nocturnal asthma symptoms as inaccurate perception occurs more frequently in association with nighttime symptoms than daytime symptoms. Nighttime symptoms are experienced in 47-67% in patients with asthma, yet many of them do not report the symptoms to their providers. Patients' perceptual ability to detect asthma exacerbations in most cases is simply based on daytime symptoms, and nocturnal symptoms are often omitted when patients report their symptoms. Similarly, adolescents with a longer duration of asthma are more likely to experience nighttime symptoms, yet they fail to recognize the symptoms as an indication of poorly controlled asthma. A high level of nighttime wheezing is detectable in children with untreated asthma including those with mild asthma and normal spirometry. Worsening of asthma symptoms often occurs during nighttime as substantial increase in airflow obstruction is detected during sleep. Nighttime symptoms not only impair sleep quality but continue to affect daytime activity level and other psychosocial functioning including learning and behavioral difficulties. Because direct monitoring of nighttime symptoms is difficult, some suggest the use of indirect indicators such as a diurnal variation of >20% in peak expiratory flow rate (PEFR) (the "morning dip") and symptom diaries. It has been reported that the Forced Expiratory Volume in 1 Second ($FEV_1$) of patients with nighttime symptoms was 31% lower in the morning than the previous evening. Nighttime symptoms are more indicative of poorly controlled asthma and have a substantial impact on quality of life. Nonetheless, direct assessment of the presence or severity of nighttime symptoms has been elusive. There is a need for a simple, reliable and quantifiable tool enabling nighttime symptom monitoring to accurately gauge the degree of asthma control as well as the response to treatment.

It is particularly concerning that children with a higher level of asthma severity are more likely to underestimate symptoms than those with lower levels (e.g., mild/moderate persistent asthma). Diminished or impaired symptom perception occurs particularly in those with high bronchial responsiveness (more inflammation), low baseline $FEV_1$ and persistent airway inflammation. Children with a history of life-threatening asthma have substantially reduced perceptual sensitivity to increased inspiratory resistive loads in a laboratory setting. Failure to recognize deteriorating asthma is, therefore, often accountable for serious health consequences including life-threatening asthma attacks and death in children and adolescents because of failure to take timely treatment actions. In summary, inaccurate symptom perception and downplaying asthma symptoms are common in children and adolescents and a major impediment to adequate management, leading to functional impairment, high asthma morbidity, and acute care utilization. Therefore, it is advantageous to provide a monitoring strategy that ensures accuracy and objectivity while increasing children's and adolescents' continual attention to symptoms over time.

Having acknowledged the limitations of symptom-based monitoring as subjective in nature, some researchers have attempted to enhance the accuracy of home-based symptom monitoring with objective and more reliable measures using Peak Expiratory Flow Meters (PEFMs). Use of PEFMs is particularly recommended for patients who suffer from a high level of asthma severity because of the greater likelihood of diminished symptom perception. PEFMs measure the Peak Expiration Flow Rate (PEFR), which is one measure of how well air moves out of the lungs during forced expiration, and can detect airway constriction before symptoms occur. Others challenged the predictive power of PEFR and viewed PEFR as a late indicator of loss of asthma control, occurring at the same time as symptoms. Studies have not reached consensus regarding clinical usefulness of PEFR on asthma outcomes. Some supported the positive effects of PEFR monitoring as reflected in reduced asthma severity scores and asthma symptoms, missed school days and health care utilization for asthma-related episodes in children and adolescents. The major merit of PEFMs is objective symptom monitoring that enables children to monitor their asthma condition in a more concrete way and to reinforce self-management through tangible changes in numeric values. They may feel more in control of the disease and empowered in communicating with providers about the degree of symptom control and the effect of their treatment. Parents notice that peak flow monitoring promoted their children's confidence in asthma self-management.

On the other hand, many studies have failed to demonstrate beneficial effects of PEFR that are superior to simply using individuals' subjective symptom-based monitoring. Confirming the reliability of PEFR values has been an ongoing challenge as values vary a great deal depending on the types of PEFMs being used or show a striking lack of association with other indices of disease activity such as $FEV_1$, bronchodilator response, asthma severity scores and quality of life. Effectiveness of the PEFM in children and adolescents is particularly hampered by users' poor adherence and inadequate techniques, and the effort-dependent nature of the method. Many researchers have also been concerned about questionable long-term sustainability of PEFR monitoring, inaccurate readings and/or fabricated readings. Overall, inconclusive improvement in asthma outcomes, unconfirmed reliability and difficulties in maintaining patient compliance and data integrity greatly undermine the clinical usefulness of peak flow monitoring. Therefore PEF monitoring can be an unnecessary burden for children and parents as well as for providers responsible for education in the proper use of the PFM when evidence fails to render sufficient clinical justification.

In sum, the bulk of the available evidence, including a recent Cochrane review, concur that PEFR monitoring provides few benefits over self-monitoring of asthma symptoms and confers little or no improvement of asthma exacerbations or control among children. Simultaneously, literature has cautioned about the likelihood of inaccurate symptom perception particularly in those who experience chronic asthma, higher levels of asthma severity and/or nighttime symptoms. Having acknowledged the dilemma, researchers have identified a specific need for alternative strategies that address the shortcomings of existing methods and enhance accuracy, objectivity and sustainability for continuous monitoring of symptoms in children and adolescents.

The following table is a listing of spirometric tests with an associated abbreviation and description of the test.

| Explanation of common test values in spirometric tests | | |
|---|---|---|
| Abbreviation | Name | Description |
| FVC | Forced Vital Capacity | This is the volume of air that can forcibly be blown out after full inspiration, measured in liters. |
| $FEV_1$ | Forced Expiratory Volume in 1 Second | This is the maximum volume of air that can forcibly blow out in the first second during the FVC manoeuvre, measured in liters. Along with FVC it is considered one of the primary indicators of lung function. |
| $FEV_1/FVC$ | FEV1 % | This is the ratio of $FEV_1$ to FVC. In healthy adults this should be approximately 75-80%. In obstructive diseases (asthma, COPD, chronic bronchitis, emphysema) $FEV_1$ is diminished because of increased airway resistance to expiratory flow and the FVC may be increased (for instance by air trapping in emphysema). This generates a reduced value (<80%, often ~45%). In restrictive diseases (such as pulmonary fibrosis) the $FEV_1$ and FVC are both reduced proportionally and the value may be normal or even increased as a result of decreased lung compliance. |
| PEF | Peak Expiratory Flow | This is the maximal flow (or speed) achieved during the maximally forced expiration initiated at full inspiration, measured in liters per second. |
| FEF 25-75% or 25-50% | Forced Expiratory Flow 25-75% or 25-50% | This is the average flow (or speed) of air coming out of the lung during the middle portion of the expiration (also sometimes referred to as the MMEF, for maximal mid-expiratory flow). In small airway diseases such as asthma this value can be reduced, perhaps <65% of expected value. This may be the first sign of small airway disease detectable. |
| FIF 25-75% or 25-50% | Forced Inspiratory Flow 25-75% or 25-50% | This is similar to FEF 25-75% or 25-50% except the measurement is taken during inspiration. |
| FET | Forced Expiratory Time | This measures the length of the expiration in seconds. |
| SVC | Slow Vital capacity | Maximum volume of air that can be exhaled slowly after slow maximum inhalation. |
| TV | Tidal volume | During the normal, tidal breathing a specific volume of air is drawn into and then expired out of the lungs. This volume is tidal volume. |
| TLC | Total Lung Capacity | Maximum volume of air present in the lungs. Effectively the Vital Capacity plus residual volume. |
| DLCO | Diffusing Capacity | The carbon monoxide uptake from a single inspiration in a standard time (usually 10 sec). This can pick up diffusion impairments, for instance in pulmonary fibrosis. This should be corrected for anemia (because rapid CO diffusion is dependent on hemoglobin in RBC's a low hemoglobin concentration, anemia, can reduce DLCO) and pulmonary hemorrhage (excess RBC's in the interstitium or alveoli can absorb CO and artificially increase the DLCO capacity). |
| MVV | Maximum Voluntary Ventilation | A measure of the maximum amount of air that can be inhaled and exhaled in one minute, measured in liters/minute. |

Results are usually given in both raw data (liters, liters per second) and percent predicted: the test result as a percent of the "predicted values" for the patients of similar characteristics (height, age, sex, and sometimes race and weight). The interpretation of the results can vary depending on the physician and the source of the predicted values. Generally, results nearest to 100% predicted are the most normal, and results over 80% are often considered normal. However, review by a doctor is recommended for accurate diagnosis of any individual situation.

In adolescence, asthma-related responsibility including symptom monitoring is being transferred from parents to children, and parents are no longer a reliable source of information for their children Therefore, health care providers need to empower adolescents in a way that helps them participate in their asthma management as a responsible party. Enabling adolescents to monitor asthma symptoms in an accurate and object manner is the first and the most important step to building partnerships between patients and providers. To ensure the partnership, the asthma monitoring strategy needs to be able to blend in adolescents' daily life and minimally compromise their sense of normalcy. Simultaneously, the approach should help providers base their treatment decisions on more objective and comprehensive data, instead of subjective or incomplete self-report.

Several researchers in Europe have investigated potential approaches to numeric representation of asthma symptoms, primarily wheezes. Some patients with severe airflow obstruction may not present with wheeze, and for those patients wheezing monitoring may not be an adequate indicator of asthma severity. Nonetheless, for the majority, wheezing is a prominent manifestation. Wheezes are adventitious sounds caused by turbulence of airflow and vibrating airway walls during airway obstruction. Audible wheezes in the respiratory sound are associated with airway obstruction. To quantify wheezes, spectral characteristics of breath sounds have been examined using computer assisted technology. A seminal attempt to quantify wheeze used an electronic stethoscope and a cassette recorder to capture wheezing for a few brief seconds before and after bronchodilator treatment. The researchers observed that reduced proportion of wheeze during the given respiratory cycle and the sound frequency of wheeze were significantly associated with the improvement in $FEV_1$ as a result of the treatment. High-pitched wheezes present with frequencies higher than 500 Hz.

Another researcher demonstrated that the frequency of the mean breath sound spectra was higher in asthma patients than control patients with normal pulmonary function, and that the frequency profile of breath sounds in asthma patients (no active wheezes) markedly differs from that of patients with Chronic Obstructive Pulmonary Disorder (COPD). Validity and reliability of wheeze sound analysis have been supported as a marker of airway obstruction, thus diagnosing asthma. A significant relationship between the presence of wheeze and a reduction in $FEV_1$ of >20% in children has been documented. Strong negative correlations were found between $FEV_1$ and the number of wheezes as well as wheeze sound quality (i.e., median frequency of the power spectra computed from expiratory sounds). One report showed high sensitivity (82%) and specificity (92%) of the presence of wheeze for a reduction in PEF of >20%. Of the many characteristics of wheezes (e.g., amplitude, frequency range, number of simultaneous wheeze, etc.), duration of wheeze was found to be the best parameter reflecting other clinical indices of asthma severity.

A technique has been developed for recording using a microphone attached to the skin of the trachea and analyzing wheezing during forced exhalation by an algorithm in a frequency-time space. The technique was able to differentiate between asthma patients and the healthy group by effectively detecting the frequency (Hz) of wheezes. Most wheezes have spectrum peaks with frequencies below 2 kHz, and mean frequencies between 200 and 800 Hz in adult patients. Global shift of the sound power distribution to higher frequencies is indicative of airway obstruction, reflected in a significant reduction in lung function. Continuous recording of wheezing using a tracheal sound recording system demonstrated its value in detecting asthma exacerbations in children and adolescents in the home environments. In the study, subjects wore a microphone for 3 consecutive days and were asked to remain in the vicinity of the receiver. The study identified fluctuating patterns of airway obstruction and found that wheezing is more evident during nighttime compared to daytime. Having understood the fluctuating nature of airway obstruction throughout the day, some have advocated for continuous monitoring of wheezing sounds given the abundance of useful information that it can generate to help providers make informed decision regarding treatment.

Compared to wheezing, cough has received less systematic attention in relation to asthma and its monitoring as assessment of cough is not a standard procedure in challenge tests. Complaints of persistent cough are common in children and adolescents with asthma, which is more apparent during exacerbations. Most cough occurs in the early morning in the first few hours after waking. As with wheezing, cough is poorly perceived by patients despite its more distinctive feature. Studies report poor agreement between self-reported and objective assessment of coughing in children. Conflicting evidence has been reported regarding the significance of coughing as an important measure in determining asthma control. One report found associations between overnight cough and reduced evening peak flow and reduced $SaO_2$, yet no relationship was found between night cough and daytime indices of spirometry abnormality although children with more severe daytime symptoms had significant night cough.

In a laboratory histamine challenge test, the frequency of cough did not show meaningful association with $FEV_1$, wheezes, dyspnea, and severity of asthma. Similarly, another study measuring cough in a natural setting using tracheal sounds recording showed that presence and frequency of cough were independent of PEFR, presence of wheeze, and self-reported dyspnea. The same study reported relatively high diagnostic sensitivity of cough for wheezes and a reduction in PEF >20% while its diagnostic specificity was poor. Few efforts have been directed at measuring cough with an objective method. For instance, LR 100 is a multiparametric recording device, worn in a waist bag, and connected to the chest by a microphone and three electromyographic (EMG) leads that capture rapid abdominal wall muscle movements. For this device, cough is defined by rapid phasic bursts of signals from the EMG leads and an audio signal from the microphone. Another attempt to measure cough used a tracheal sound recording system that consisted of a microphone, transmitter, receiver and recording equipment. In both methods, the devices consist of many parts that need to be attached to the body and/or carried by patients; so it may not be suitable to a real life situation. Moreover, analysis and interpretation of collected data requires expertise and it is laborious and time consuming as it involves hours of visual inspection and/or hours of listening to recorded sounds.

Taken all together, cough is modestly predictive of asthma exacerbations, and recent literature established that the majority of children with isolated cough do not have signs of typical asthma inflammation and response to steroid treatment. Thus, cough alone may not be useful for diagnosing asthma or assessing asthma control. However, examining coughs within the context of other symptoms such as wheezes and activity limitation in confirmed cases of asthma may add more detail information in determining the degree of asthma control because for some children and adolescents with asthma, persistent cough can be the only symptom during airway obstruction. Therefore, it seems advantageous to develop a comprehensive strategy that can capture these cardinal signs of asthma accurately and objectively.

An antecedent to successful asthma management is a patient's ability to accurately identify symptoms. Individual capacity to recognize symptoms relies on perceptual sensitivity, vigilance and recollection and thus is subject to bias. Because of the subjective nature of symptom assessment, the literature has consistently raised concerns about inaccurate symptom perception in children, particularly adolescents with asthma and its implication for inadequate asthma management. To offset inaccuracy of symptom perception and unreliable symptom reports, home monitoring of PEFR has been recommended. However, erroneous report, poor adherence and its insensitivity to airway changes have undermined PEFR's clinical usefulness and complicated clinician's decision about planning and adjusting asthma management protocols. For this reason, many researchers and clinicians advocate symptom-based monitoring while purporting the need for strategies to maximize the accuracy and efficacy of patients' symptom monitoring.

Wheezes and cough are the acoustic manifestations of airway obstruction that can be recorded and monitored using a noninvasive method that requires minimal patient cooperation during both day and night. To date, breath sound spectral analysis has demonstrated a potential for a new non-invasive method for monitoring of asthma. The earlier efforts to quantify asthma symptoms have concentrated on wheezing while paying little attention to other important hallmark symptoms such as coughing and activity limitations. In most cases, the quantification was attempted in laboratory settings for a short period of time and/or restricted mobility of subjects due to the technical requirements of the monitoring equipments. Analysis and interpretation of recorded data are not always intuitive and entail complex and time-intensive procedures. In addition, the previous attempts have not clearly delineated the way in which the quantified information is translated into clinical practice to improve asthma management by patients and providers and ultimately asthma-related outcomes. Because of the delay between symptom occurrence and analysis, the existing quantification methods have limited clinical utility in guiding patients and providers to strategize management plans in a timely fashion. These limitations identified in the current literature show a need for innovative approaches that enable continuous accurate monitoring of asthma symptoms of different types (e.g., wheezes, cough and activity levels) simultaneously with a concrete application for asthma management for patients and providers.

Having acknowledged the challenges in and needs for reliable asthma monitoring, the disclosure herein provides a non-invasive approach to aid patients in assessing daily symptoms by applying automated sound-detection and analysis technology. This enables long-term monitoring of the disease with minimal inconvenience to the patients.

The automated device for asthma monitoring (ADAM) is a portable system that monitors both the breathing and movement of the patient and, through the application of analog and digital signal processing, discriminates between 'symptoms of interest', which are sonic events that may be coughing or wheezing or other symptoms associated with the assessment of asthma, and other sonic events such as speech, door slamming, phones ringing, and other background sounds. Symptoms of interest are related to cardinal symptoms of asthma-wheeze and cough, including nighttime symptoms. The device's accurate and detailed monitoring of asthma symptoms is based on technology that captures and integrates multidimensional elements of asthma symptoms including frequency, intensity, duration and timing of breathing and associates these sounds with a measurement of the duration and intensity of physical activity.

The device can be programmed with an algorithm that automatically converts complex raw data in the form of wave spectra into more intuitive numeric data that can be readily translated into information meaningful to patients and clinicians (i.e. the numbers of cough and wheezing episodes during night time). Because the algorithm can be applied in a consistent manner, collected information is deemed more objective and reproducible. The device can enable the detection of trends identifying the timing and distribution of asthma symptom activity during day and nighttime. Particularly, the new device is useful for the continuous and intense monitoring at nighttime. Capacity to observe nighttime symptoms is of particular value because such symptoms are often overlooked by patients despite its clinical significance in informing the symptom severity and response to treatment.

The ability of the device to measure motion allows it to monitor the levels of physical activity that can help estimate functional limitations due to asthma and afford the opportunity to precisely evaluate symptoms in the context of physical activity. This data may be downloaded by the patient's doctor to help guide the patient in setting appropriate limitations.

By employing a mobile device such as a cell phone as the basic platform, the device may not draw attention to the user, which can be an important factor for users in the target age group. Such aesthetic features can save users from embarrassment by wearing the device, thereby effectively encouraging the daily use of the device. In addition, an embodiment where the entire system is built into a regular mobile phone can make the system widely available at low cost and with little inconvenience to the user.

DETAILED DESCRIPTION OF THE INVENTIONS

Figure 1:
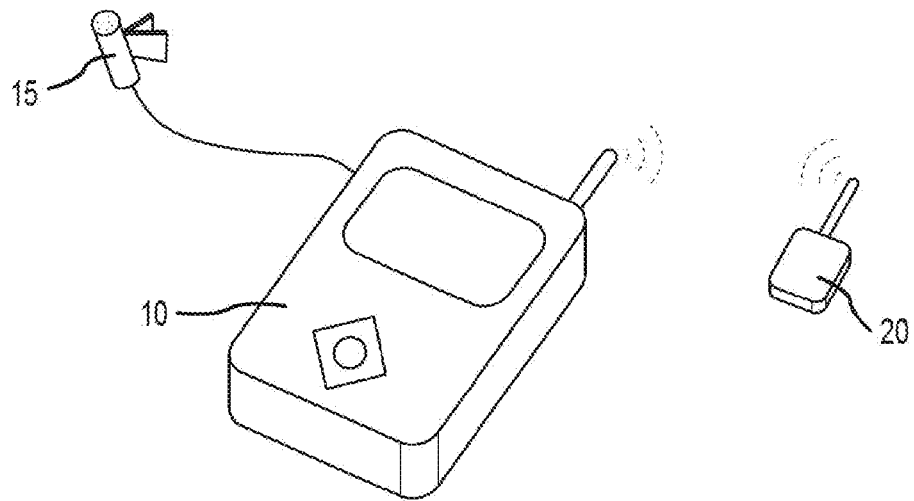
FIG. 1 shows embodiments of the system described herein.

The technical underpinnings of the proposed project are well established. Various embodiments employ a combination of off-the-shelf commercial electronic hardware and custom hardware and software. The sound data analysis techniques are well established. The novelty of the proposed project is at least two-fold. One novel feature is that the system employs multi-modal monitoring of an individual, specifically the identification of wheezing and cough from their breath sounds and measuring the level of the patient's motion and activity. Analyzing these attributes together (wheezing and cough and activity) provides a more comprehensive and greater insight into the levels of asthma control of a patient than monitoring of a single parameter (e.g., wheezes) allows. Asthma symptoms manifested as a result of vigorous activity can be differentiated from those occurring independent of physical activity changes. This system can also monitor the attributes of wheezing and cough during sleep, a capability previously unavailable with prior methods of asthma assessment. Another novel feature of this device is that it enables continuous long-term monitoring of an individual, to determine individual circadian patterns of asthma symptoms and to program the device to what is considered normal for the person based upon their past data. This enables the feedback mechanism of the device ("alarm" function) based on the established individual norm. This also can enable tracking of asthma symptoms over time to allow the health-care provider to adjust medications to their appropriate levels.

Sound recording technology and data storage have made tremendous advances in the past 10-20 years. Digital recording devices with vast storage capabilities (days of continuous recording) have shrunk to iPod size dimensions. Low-power signal processing hardware also has made tremendous strides in recent years allowing real-time analysis and reduction of data to useful information. Algorithms can be programmed into a compact digital signal processor carried by the individual that can reduce the data to simple measures such as the number and severity of coughs or the amount and severity of wheezing.

In addition to the availability of miniaturized audio recording and analysis hardware, speech and sound analysis methods have greatly increased in sophistication and effectiveness in recent years. Speech recognition algorithms employing Hidden Markov Models have reached a practical level of performance (80%-98% accuracy) depending upon background noise levels among other factors, and multimodal recognition schemes employing both sound and visual analyses perform even better. The fundamental methods employed in speech recognition have not changed significantly for the past decade or more. Typically the speech signal is discretized, i.e., divided into short time segments of 10 milliseconds or so, and the frequency content of each time-slice of sound is characterized by a low-dimensional set of real numbers (a vector). A popular method employs the so-called "cepstral coefficients" which are computed as the Fourier transform of the log-magnitude of the sound spectrum. The "cepstrum" is a compact way to represent the frequency content of a sound and its value, which is able to discriminate between different types of sounds. For example, pitched speech sounds, such as long vowels, have the majority of their signal power in harmonically related peaks while consonant sounds such as "s," "t," "p," etc. display a sound spectrum with power more evenly distributed over the audio frequency range. Cepstral analysis enables the researcher to effectively discriminate such sounds, and hidden Markov model techniques allow recognition of sequences of fundamental sound elements as they form phonemes and words, ultimately allowing the spoken words to be identified. These same techniques are the foundation for algorithms to discern coughing from speech and backgrounds sounds and to detect wheezing as compared to normal breathing.

One technique for detecting wheezing uses a microphone attached to the skin of the trachea and detects wheezing during forced exhalation by an algorithm in a frequency-time space. The technique is able to differentiate between asthma patients and the healthy group by effectively detecting the frequency (Hz) of wheezes. Most wheezes have spectrum peaks with frequencies below 2 kHz, and mean frequencies between 200 and 800 Hz in adult patients. Global shift of the sound power distribution to higher frequencies is indicative of airway obstruction, reflected in a significant reduction in lung function. This research provides a starting point for the portion of the algorithms of ADAM that relate to the detection and categorization of wheezing.

The device can have a capacity to bring about patient behavior changes such as avoiding triggers and adjusting medications as the device can provide the opportunity for in-time review of symptoms. In addition, the long-term monitoring of a patient can enable recognition of deteriorating asthma symptoms, which can cause the device to automatically send out signals (alarm) to patients so that appropriate and timely intervention can be initiated by either the patients or health care providers.

The application of this device is not restricted to the specific population. The device is potentially applicable across the lifespan after the establishment of age-specific parameters of asthma symptoms. In that sense, the device can be a more sensitive measure of asthma symptoms reflecting age differences. A single device could be pre-programmed with age-specific algorithms for asthma symptom monitoring, which could then be easily age customized at the press of a button. Recording over longer periods can aid understanding on the long-term trajectory of the disease. The implications of the device for those who present with limited capacity to verbally communicate their asthma symptoms such as young children and cognitively challenged individuals are also significant.

The mock clinical scenario presented below demonstrates the potential for a real clinical scenario to be combined with the application of the ADAM device envisioned by the investigators. JC is a 16-year-old boy with moderate persistent asthma and a history of several emergency visits for asthma each year. His provider had prescribed a daily controller medication for him (fluticasone propionate, 220 mcg 2 puffs BID), but he rarely uses it because he has not perceived any significant benefit. He reports not sleeping well, which causes him to feel poorly rested in the morning. He is on the track team, but feels his performance has not been optimal lately. He relies heavily on albuterol, with several self-administered doses each day. After a discussion with his provider, JC agreed to wear ADAM for 7 days. At a follow-up visit the next week, the provider and JC reviewed the symptom pattern displayed on the screen of the mobile phone monitor. Data from the device revealed significant wheeze and some cough, predominantly at night. After discussing the results, JC agreed to use fluticasone daily to see if the symptoms improve. After 1 month, JC repeated his symptom monitoring with ADAM, and discovered his wheezing and coughing events were significantly decreased as compared to the prior monitoring period. In addition, JC was alerted by ADAM when his asthma became out of control, which allowed him to take precaution and follow closely his asthma action plan. JC felt that he was sleeping better and his performance in track had improved. He agreed to continue to use fluticasone for another 2 months, and to use the symptom monitoring device intermittently to help track his symptoms.

The device is a biobehavioral instrument in which accuracy, in many instances, is of paramount importance. Accuracy describes how closely a measurement reproduces the value of the attribute being measured, that is a true value. Sensitivity and specificity are methods to gauge the accuracy of the measure. Sensitivity is defined as the probability of a positive test results when the condition is present, while specificity describes the probability of a negative test results when the condition is absent. The sensitivity of the device would be demonstrated when it yields data indicating the presence of asthma symptoms in asthma patients. Specificity would be supported when the device generates negative outcomes in those without asthma. Definitive sensitivity and specificity are not attainable due to the error component that is inevitable in reality. Signal Detection Theory (SDT) has been adopted in developing assessment and decision systems to minimize the error while enhancing accuracy and discriminatory power in the presence of some uncertainty. SDT provides methods that assist a reasonable decision making process through a precise language and graphic notation. SDT methods partition the variability in the data produced by assessment systems into two components: perceptual and decisional. The perceptual component represents quantitatively (i.e., sensitivity and specificity) how well the system discriminates between two possible states (e.g., presence or absence of asthma symptoms). The decisional component, on the other hand, represents the position of the cutoff score employed to arrive at the discriminations. SDT offers the decisional component that is not confounded by changing cutoff values or numbers of positive cases (e.g., asthma diagnosis). SDT estimates accuracy by analyzing the receiver (or relative) operating characteristic (ROC) that was originally developed by electrical engineers. ROC curves quantify a pure index of accuracy (Area Under the ROC curve: AUC value) that demonstrates the limits of a measurement's ability to discriminate between alternative states (e.g., asthma diagnosis vs. no asthma diagnosis). Several ROC curves and their corresponding AUC values (ranges from 0 to 1; higher values indicate better discriminatory power, that is higher accuracy) for multiple measures can be generated for comparison.

Validity represents how well the measured variable represents the attribute being measured. Three types of validity have been defined: content, criterion and construct validity. Content validity, indicating how well the items in a test reflect the entity being measured is often examined in psychometric assessment tools. Content validity of the new device can be supported by the scrupulous process of parameter identification of asthma symptoms to ensure that the information collected through the device adequately reflects the asthma status of an individual. Criterion validity including concurrent and predictive validity indicates whether the instrument correlates highly with other measures of the same object or event. Ideally, the other measures include an accepted gold standard against which the proposed measure can be assessed. Criterion validity is considered existing when the results from a measurement are highly correlated with those from a tool with established validity. The criterion validity of this device can be established by comparison with other established measures of asthma monitoring including FEV1, FeNO, and daily symptom diary, or other indicators of asthma condition such as quality of life and health care utilization. Significant correlations with these measures provide evidence for the criterion validity of the device. Construct validity focuses on the ability of the instrument itself to measure the trait or characteristic of interest and function in accordance with the purpose for which it is being used. A contrasted-groups approach can be used to generate support for construct validity of this device by comparing the results of the device from an asthma group and their non-asthma counterparts and determining that the output values and patterns clearly and effectively differentiate the asthma group from the control group.

The algorithms embedded in this device employ both frequency and time domain analyses. A time domain algorithm is used to detect rapid sound level changes that may be associated with coughing or wheezing or could be a background noise such as a door slamming. The sound clips that contain these rapid sound level changes become candidate events that can be confirmed as a cough by further analysis in the frequency domain.

Frequency domain analysis of the harmonic content of candidate sounds is employed to discriminate symptoms of interest from other sonic events, such as speech, door slamming, phones ringing and other background sounds. Wheezing displays a relatively limited number of harmonics while speech shows a richer harmonic structure and coughing is nearly devoid of any harmonic structure, thus allowing these sounds to be distinguished from each other.

FIG. 1 shows embodiments of a baseline system comprised of individual elements. The microphone, or detector 15, is a clip-on wired microphone, such as the Shure WL93 Lavalier Microphone, connected by a wire to a base unit 10 which, in this embodiment, is a battery-powered handheld computer. The activity data may be collected by any of a number of activity detectors 20 (e.g., accelerometers), such as the Dynastream AMP® unit. These units have the capability of either storing the data for later download or wireless sly transmitting the data to the base unit 10.

Figure 2A:
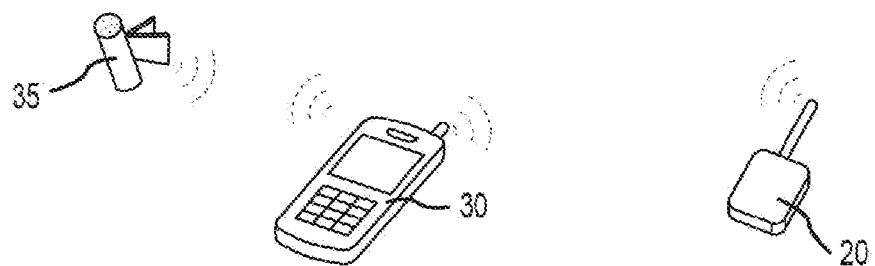
FIG. 2A-2D show embodiments of the system described herein.

FIG. 2A shows an embodiment where the main computer has been replaced by a cell phone, although it could be any portable computing device 30 such as a personal digital assistant (PDA), handheld computer, pager, or portable media player. The microphone has been replaced by a wireless microphone or detector 35 that communicates wirelessly with the computational module in the cell phone. This wireless link could use any of a variety of available technologies including Bluetooth, ZigBee, wireless USB, and proprietary systems.

Figure 2B:
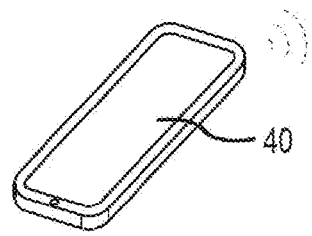

FIG. 2B shows another embodiment where the computational module, speaker, microphone and accelerometer have all been incorporated into a single device 40. The Apple® iPhone® is an example of a commercial device that incorporates all of these elements.

Figure 2C:
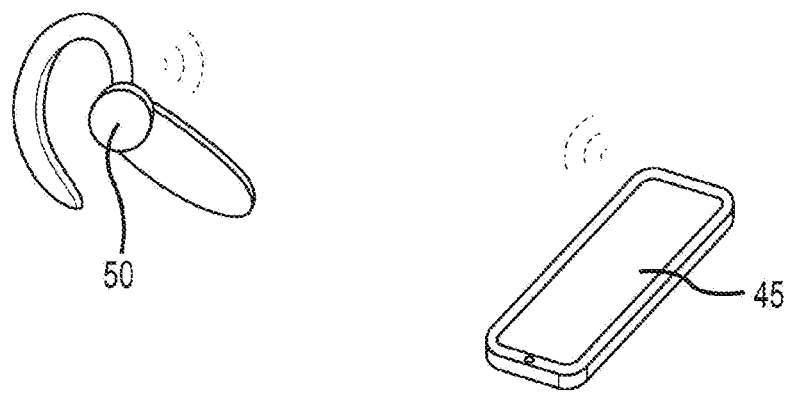

FIG. 2C shows yet another embodiment where the microphone and the speaker are part of a separate device 50 that communicates wirelessly with a computational module 45. Certain embodiments of this separate device are referred to as headsets or earpieces and are commercially available for use with the telephone function of a cell phone. This system may enable the deployment of ADAM as a pure software offering compatible with a wide range of standard cell phone and accessory hardware.

Figure 2D:
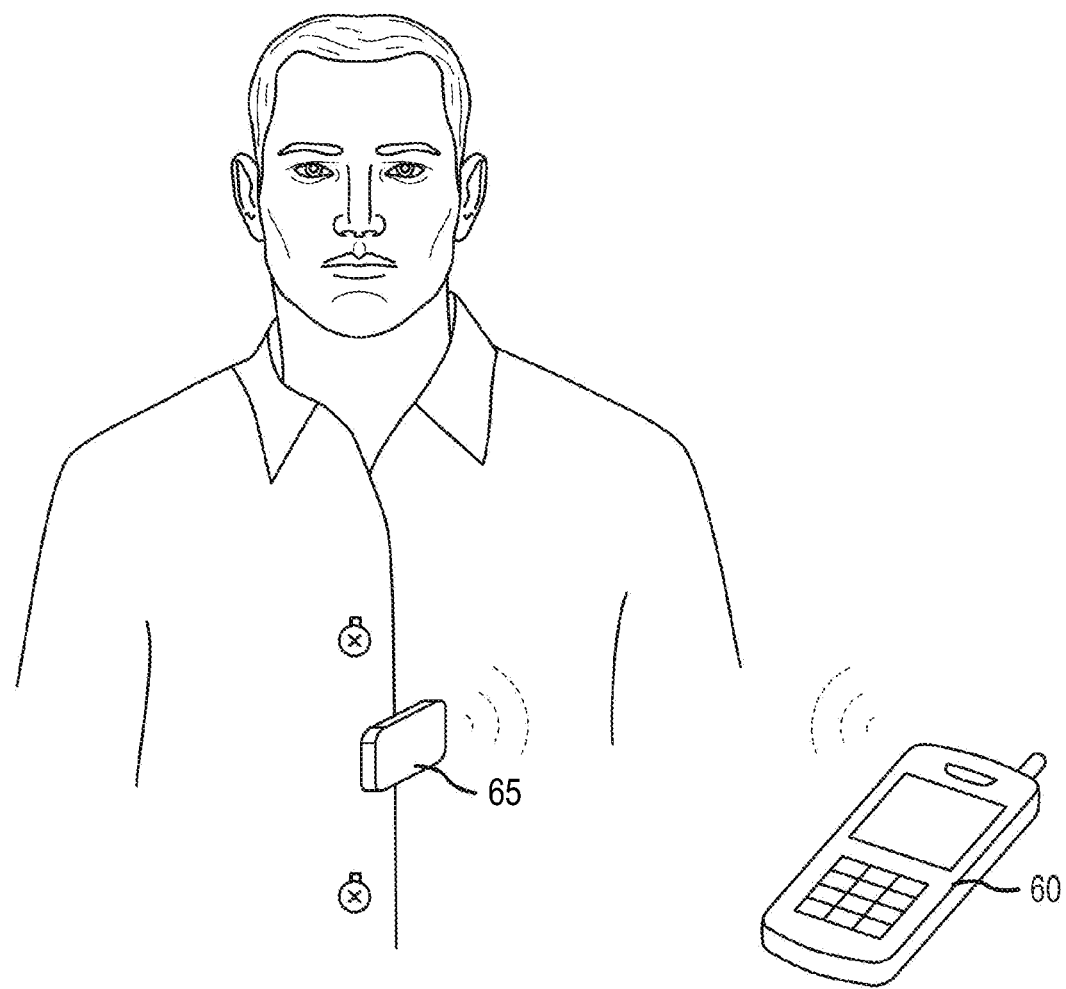

FIG. 2D shows a standard cell phone 60 with a separate device 65 that contains both a microphone and an accelerometer. Advantages of this embodiment are that the microphone is closer to the mouth than the cell phone, which may in a pocket or purse, and can provide increased fidelity of the sound detection, and that the separate device contains all of the unique capabilities required for ADAM. The capabilities required of the base cell phone are now very standard, enlarging the population of users who already have cell phones that would be satisfactory base units.

Figure 3:
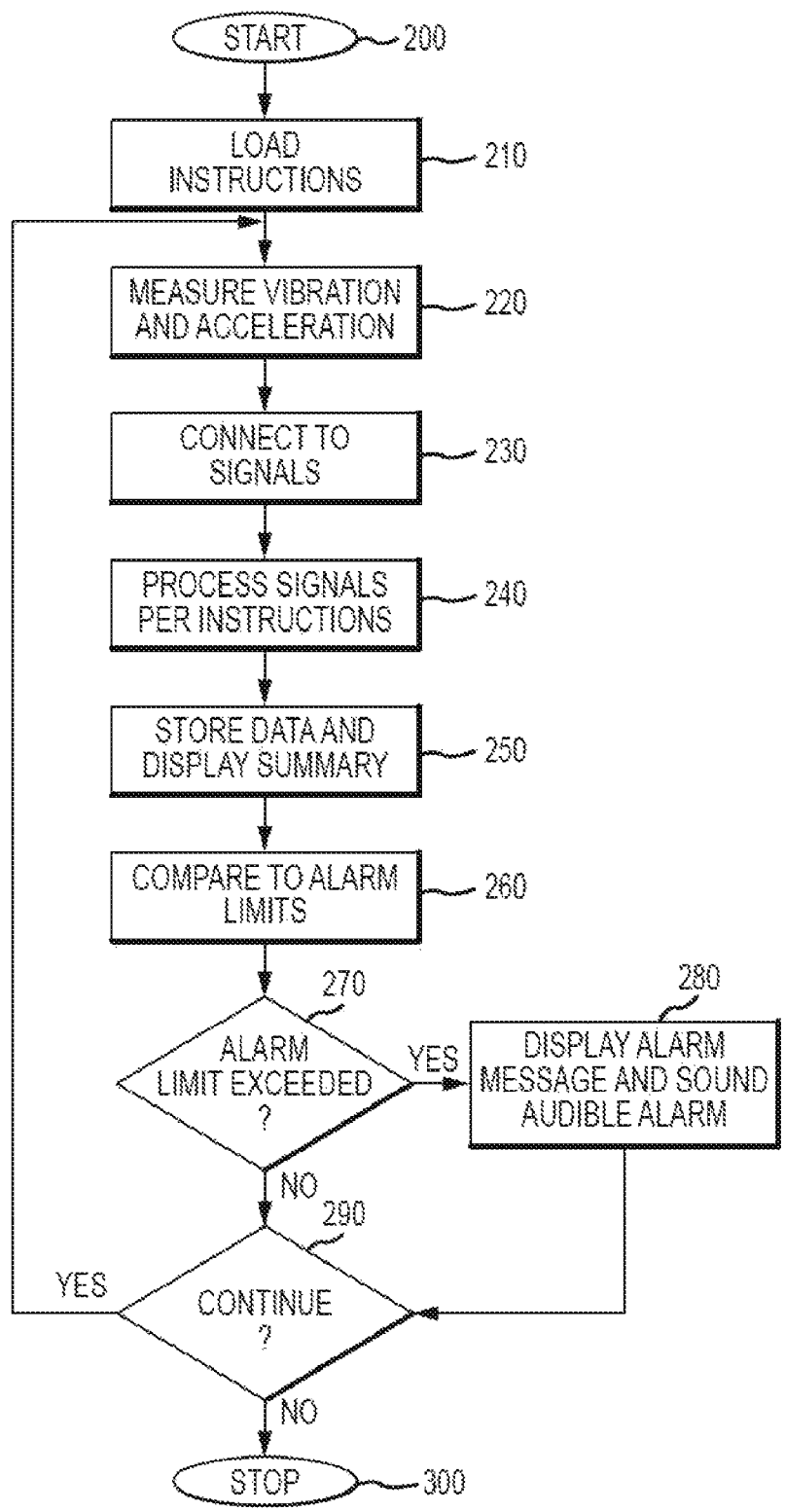
FIG. 3 is a block diagram of embodiments of the system as described herein.

FIG. 3 shows the operation of device 10 according to at least one embodiment. Step numbers are indicated in this description by parentheses. The device 10 is activated (200) and loads the instructions (210) from either local memory 110 or possibly downloads these instructions from remote system 190. The system commences measurement of vibration (sound) and acceleration (220) and conversion of these measurements to signals (230). These signals are passed to processor module 120 where the instructions are executed and the signals processed (240). As directed by the instructions, data may be stored in memory 110 or displayed on the visual output device 130 (250). Data values computed according to the instructions are then compared to alarm limits (260) and a decision is made (270). If the alarm limit is exceeded, an alarm message is displayed on visual output device 130 and an audible alarm is emitted by audio output device 180 (280). If the alarm limit is not exceeded, then the system checks to see if it should continue or whether a command to stop has been received (290). If the monitoring is to continue, then the system returns to step 220. If the system has been commanded to stop, it goes to step 300 and stops.

Figure 4:
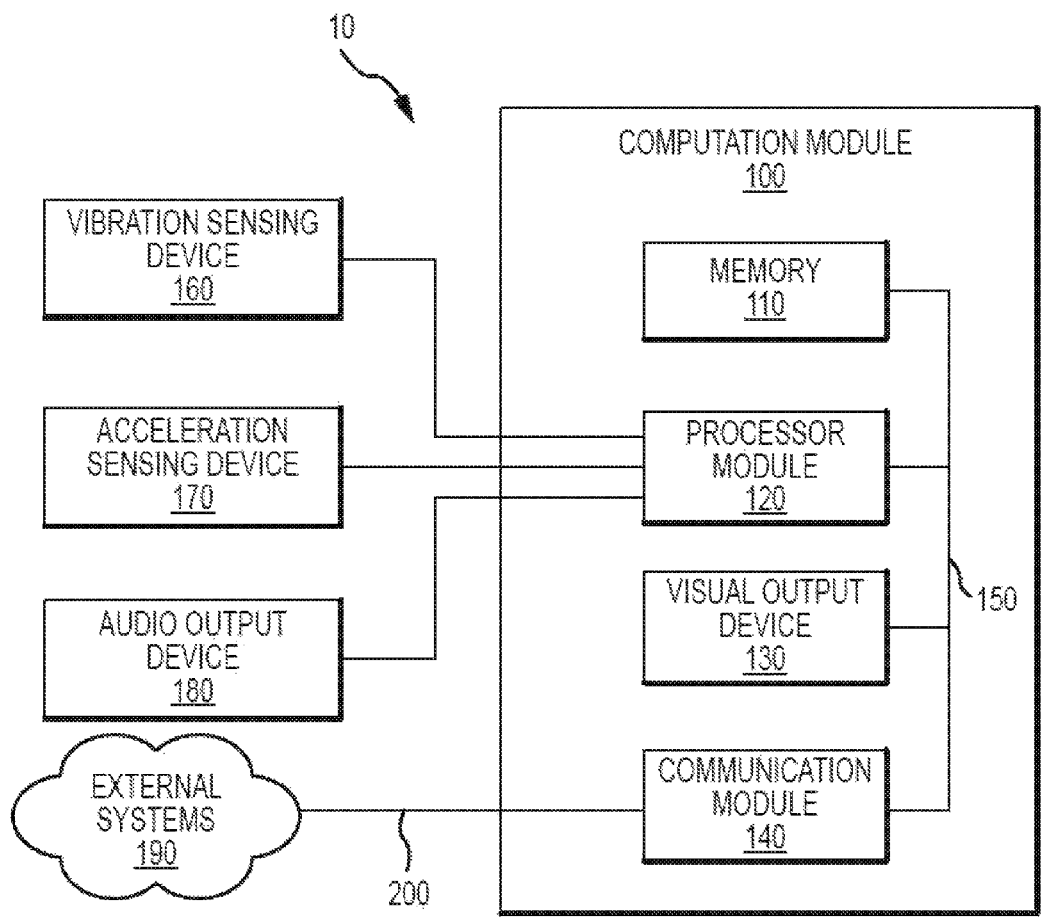
FIG. 4 is a flowchart of embodiments of the operation of the system.

FIG. 4 shows a basic block diagram of the device 10. In some embodiments, computation module 100 comprises a memory 110, a processor module 120, a visual output device 130, a communication module 140, and a communication bus 150 between the subsystems of computation module 100. The vibration sensing device 160, the acceleration sensing device 170, and the audio output device 180 are shown separate from the computation module 100 as one or more of devices 160, 170, and 180 may be physically separate from computation module 100 in some embodiments. The external systems 190 communicate with communication module 140 over a link 200 that may be wired or wireless and employ any of a number of standard or proprietary communication protocols such as Ethernet 100/1000/1G, serial, USB, wifi, ultrawideband, or zigbee.

In describing various embodiments, multiple components are used to aid in conveying the concepts. The use of these specific devices does not preclude the use of generic devices with the same function, and devices of a class may be substituted for one another within the scope of this disclosure. The generic vibration sensing device 160 is considered representative of the entire class of vibration sensing devices that can measure vibration in at least a portion of the audible spectrum as well as devices that do not sense sound directly but measure the physical vibration of a user's throat tissue. In example embodiments described herein, a microphone may be used as a representative example of the class of devices of vibration sensing device 160 without loss of generality or scope of this application. Similarly, a speaker is representative of the entire class of audio output device 180 that include buzzers, resonators, piezoelectric devices, speakers, and vibrators. Display screens are representative of the entire class of visual output device 130 including sets of one or more flashing or steady single-color or multicolor lights, text displays, and monochrome or color graphic displays. Memory 110 represents the entire class of nonvolatile and volatile data storage media, including solid state drives (SSDs), flash memory, random access memory (RAM), read-only memory (ROM), electrically erasable programmable read-only memory (EEPROM), and disk-on-chip. Processor module 120 includes all computation devices such as microcomputer, microprocessors, digital signal processors (DSPs), or special purpose processing devices implemented as application-specific integrated circuits (ASICs) or field programmable gate arrays (FPGAs). The processor module 120 may include its own memory separate from memory 110 as well as digital-to-analog (D/A) and analog-to-digital (D/A) signal conversion circuits and other analog signal processing and filtering circuitry. The links between the various blocks of system 10 may be implemented as wired connections, optical fiber, wireless RF or optical signals, or any other signal propagation technology and configured in any of a number of topologies including direct linkage, a multi-drop bus, a star network with a hub, and token ring network. Elements of functionality may be moved from one block to another in some embodiments within the scope of this disclosure. Devices and modules shown as separate blocks in this diagram may be integrated or communication lines may be consolidated through the use of signal switching devices.

Figure 5:
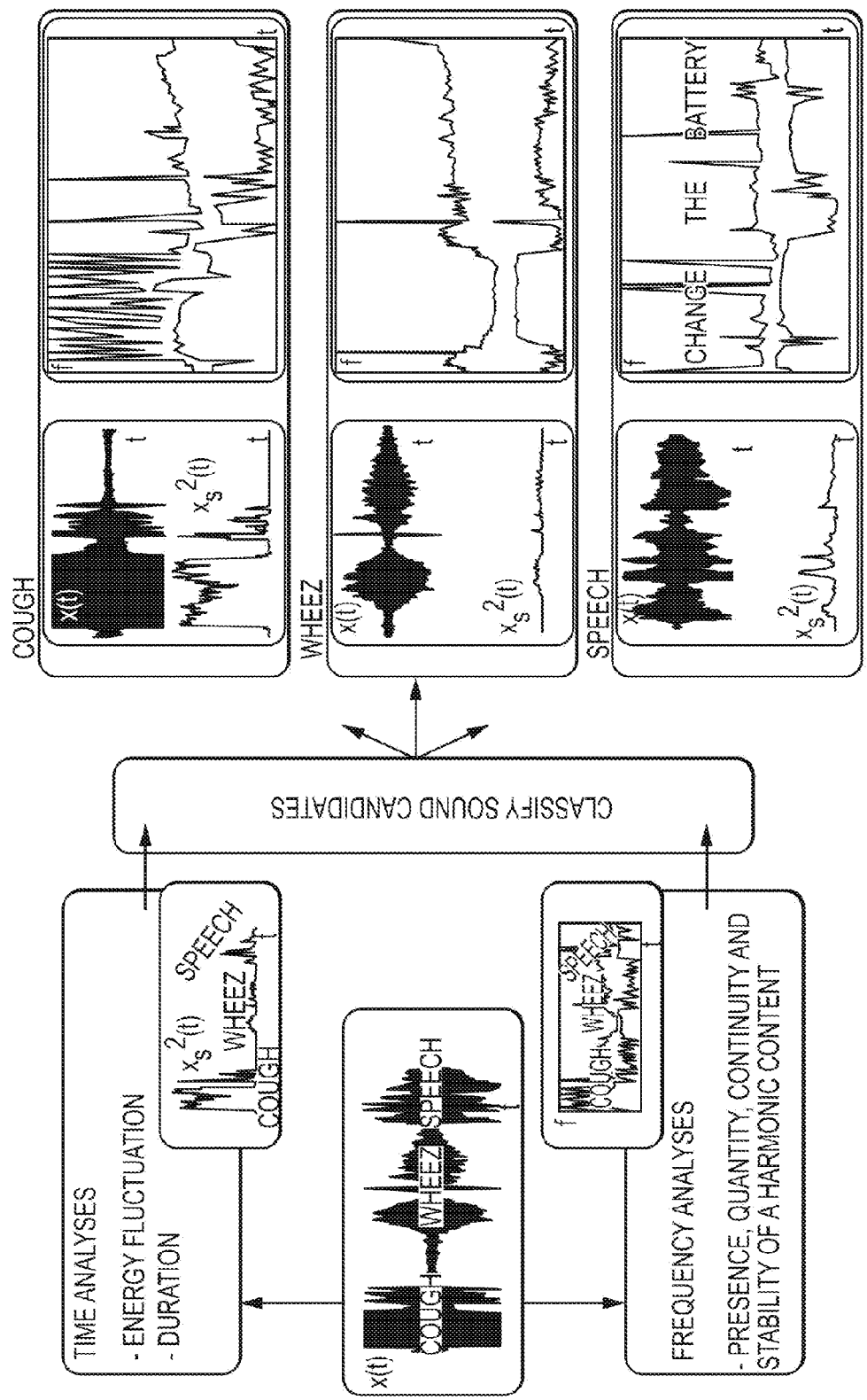
FIG. 5 contains pictures of an audio recording identifying the differences between types of sounds.

FIG. 5 includes several related plots. The black colored contour plots present time waveforms of recorded sounds (x(t)) and the averaged square (xs2(t)). The multi-line plot is the spectrogram of the recording x(t), and shows changes of the spectral power distribution over time, where peaks indicates the strength (power) of a frequency component, and the x and y axes are time and frequency, respectively.

Figure 6:
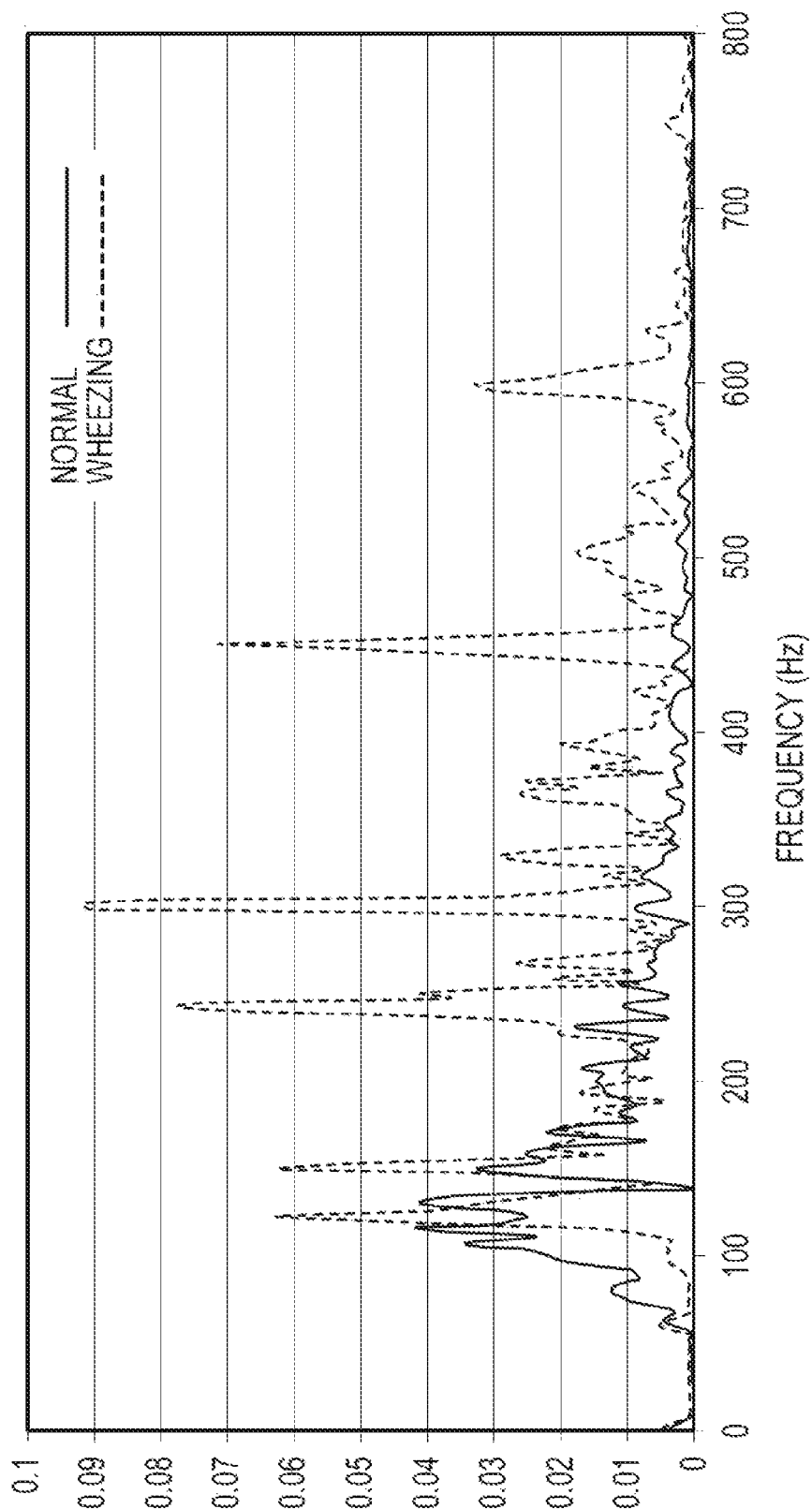
FIG. 6 is a frequency histogram comparing normal breathing to wheezing.

FIG. 6 shows the Fourier spectrum of both normal breathing and wheezing sounds. The sound clips are each of 70 millisecond duration and sampled at 4000 times per second. The pitched sound components associated with wheezing are clearly visible as large peaks in the power spectrum at 125, 150, 250, 300, 450 and 600 Hz while normal breathing is characterized by a broad spectral feature in the 100 Hz to 200 Hz range of frequencies. Conversely the normal breathing sound displays a broad distribution of power limited to a band of frequencies from 100-200 Hz. Also note that the set of peaks in the wheezing signal are not all harmonically related, i.e., they do not appear at frequencies that are all integer multiples of a low fundamental frequency, as in speech. This marked difference enables one to define a simple and easily measured metric to distinguish wheezing from normal breathing and speech as well as to characterize the severity of the wheezing.

Wheeze detection performed by a Fourier Transform-based algorithm has been previously verified and found to have sensitivity of 91% and specificity of 89% when compared with consensus assessment by a panel of experts. The Fourier transform converts the time waveform (sound pressure versus time) into a frequency representation, the sound pressure at each frequency. A pure sinusoidal tone appears as a single peak at the frequency of the sine-tone in the Fourier transform spectral representation. More complex sounds display Fourier spectra with many peaks present, such as speech, or with energy more evenly distributed over a range of frequencies, such as cough sounds. The characteristic sounds of wheezing, which nearly anyone can recognize intuitively, appear in a Fourier spectrum as a series of discrete peaks. The ability to visualize and discern different sounds in the Fourier representation makes it a powerful tool for sound recognition and classification.

A simple program that counted the number of harmonics in candidate events is able to classify sounds in time intervals when there is little background noise. Neural networks, computational models based on biological neural networks that consist of connections between basic units called neurons and their parameters, may yield better results for noisy data. In highly cluttered sound "scenes", statistical source separation techniques may aid in discriminating events of interest.

$$I = \frac{\sum \text{Power}(220 \text{ Hz} : 800 \text{ Hz})}{\sum \text{Power}(20 \text{ Hz} : 200 \text{ Hz})} \qquad \text{Equation 1}$$

Another analysis algorithm is shown in Equation. 1, which employs the integrated spectral power over different frequency bands. I is the ratio of the total power contained in a band of frequencies from 200 Hz to 800 Hz divided by the integrated power in the Hz to 200 Hz band. For the sample data shown in FIG. 6, this algorithm gives I(wheezing)=3.1 and I(normal)=0.58 which is a marked difference.

One can directly measure the integrated power spectral density over selected bands of frequencies with straightforward switched capacitor filters. These are simple integrated circuits that can operate at low power levels and provide a continuous estimate of parameters such as those defined in Equation 1. The value of this approach is that much less data need be stored. This one parameter can be measured once per second and stored as a single byte (8 binary bits) of data instead of the 8000 bytes per second of data storage that it would take to record and store the raw sound. Thus, an entire day's worth of the "wheezing index" would require only about 90 kilobytes of storage as opposed to more than 700 Mbytes of storage for one day of raw data.

Another method of detecting wheezing is to measure the spectral centroid as shown in Equation 2. Given a time domain signal x(t) and its N point discrete Fourier transform x(n), the spectral centroid is defined as follows:

$$\text{Centroid} = \frac{\sum_{n=1}^{N/2} f(n) * |x(n)|}{\sum_{n=1}^{N/2} |x(n)|} \qquad \text{Equation 2}$$

In this equation, f(n) is the frequency of the n'th bin in the Fourier transform domain and |x(n)| is the magnitude of the n'th Fourier component. The frequency of this centroid can be compared to a threshold value above which the patient is considered to be wheezing. This frequency can also be tracked over short and long time periods, as the centroid can tend to increase in frequency with increasing severity of wheezing. There may be multiple threshold levels each associated with a severity level. In addition, there also may be a threshold value for the short-term change in the centroid to monitor for a sudden increase in the severity of a patient's wheezing which may indicate a serious condition that may need immediate attention.

The width of the frequency representation of a patient's breathing that is above a threshold can also be measured as an indication of asthma. While this can tend to track an increase in the integrated power spectral density and a shift in the spectral centroid, it may be sufficient to simply monitor the total width of the spectrum where the power spectral density exceeds a threshold value.

Another method of detecting wheezing is to determine the Spectral Peaks to Noise Ratio (SPNR) as shown in Equation 3. Normal breathing sounds are characterized by broadband spectral features in the Fourier (frequency) domain whereas asthmatic wheezing is characterized by a power spectrum that exhibits a number of discrete peaks, each corresponding to a component of the pitched sound of the wheezing. The quantitative measure of this is the total power in the peaks divided by the total power in the entire spectrum. Normal breathing can exhibit a very small value of SPNR, whereas wheezing can have a larger value, approaching unity in the limiting case of extreme wheezing.

$$SPNR = \frac{\sum_{peaks} |x(n)|^2}{\sum_{n=1}^{N/2} |x(n)|^2} \quad \text{Equation 3}$$

Detection of wheezing may be further coupled with a measurement of the total duration of exhalation, with a calculation of the percentage of the duration of exhalation that is considered wheezing. This percentage can increase over the short term and long term with an increase in the severity of wheezing. The respiration rate and duration of exhalation can also be measured as parameters that provide information about the patient's condition, again especially when changes over a short period of time are compared to a baseline.

Figure 7:
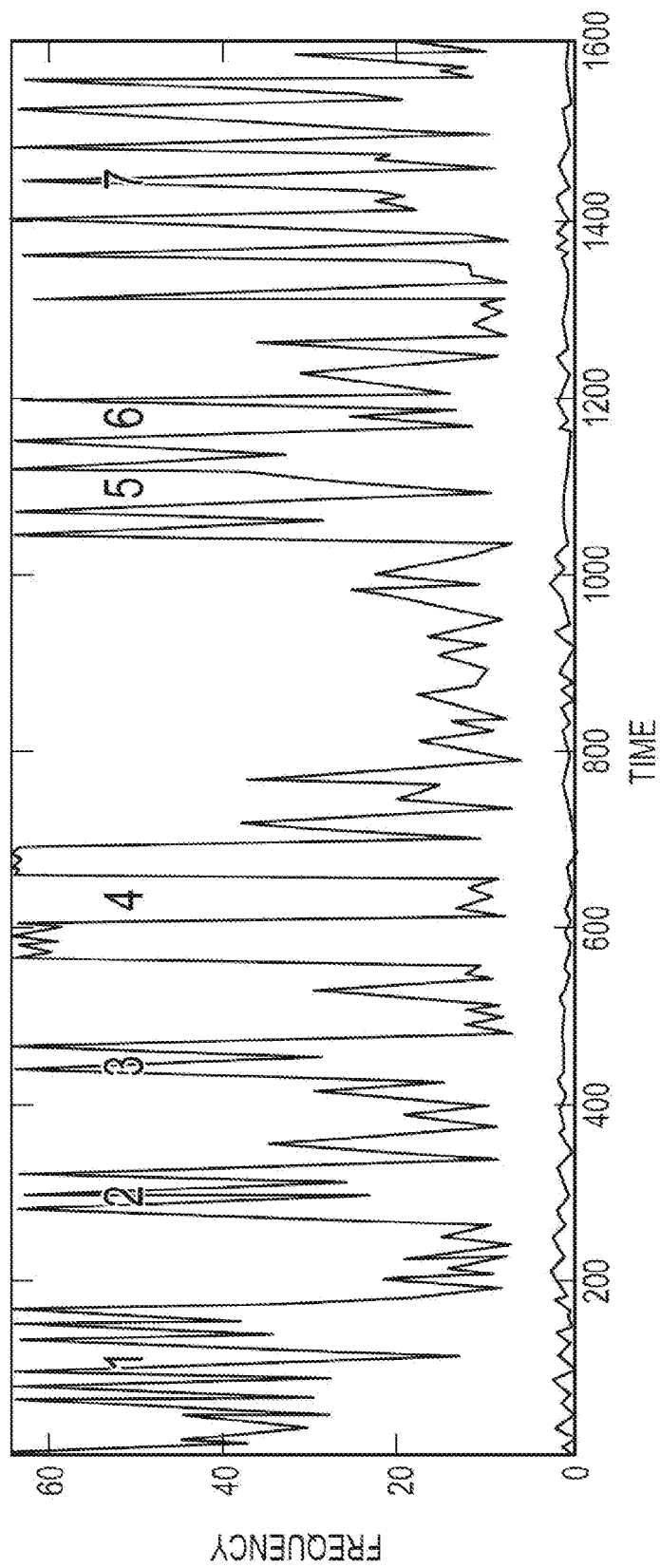
FIG. 7 is a frequency vs. time graph of a short recording including various sounds.

FIG. 7 is a spectrographic representation of a short sound segment containing speech, features (2,6,7), coughing (4), heavy breathing (3) and various background noises (1,5). The horizontal scale is the time frame number and the vertical scale is the frequency "bin" number respectively. The duration of the sound is 9 seconds and the frequency range is 0-5000 Hertz.

A cough can be distinguished from speech by the duration of the sonic event and the spectrum of the event. Speech events are longer in duration generally but most importantly contain "pitched" segments, i.e., a dominant frequency may be assigned to the sound. Coughs, on the other hand, are spectrally broad-band and generally shorter in duration. Some embodiments include an automated "cough detector" analysis program that can scan the audio to look for sonic events that exceed a set amplitude threshold. All candidate events can then be examined using short-time Fourier analysis by directly measuring the integrated power spectral density over selected bands of frequencies to determine if the spectrum has strong frequency components or if it is broad band, which would be identified as a cough. Thresholds for the amplitude, duration and spectral characteristics of a sonic event may be set to classify the event. Other embodiments may employ spectral analysis and neural network classification techniques to identify sonic events. For example, the short clip of sound shown in FIG. 7 is illustrative of the sorts of sounds that can be classified. The figure shows the short-time Fourier transform of a 9 second sound clip. The sound clip starts with background "rustling" noise from handling of the voice recorder (1). This is followed by the word "coughing" spoken by a female subject (2), which is then followed by the subject inhaling strongly (3) and then two coughs (4). A few seconds later there is more background noise (5), a barely intelligible background speaker (male) (6) and then the spoken words (female) "very strong cough" (7).

A visual inspection of the spectrogram in FIG. 7 provides an intuitive guide for the development of the automated tools. First, notice that speech events, such as event 7, display a set of peaks in the sound spectrum, appearing as horizontal lines in the spectrogram. These are distinguished from the more evenly distributed energy in the spectrum of a cough, event 4. Note also in event 3 that a normal breathing sound displays the formant structure from the subject's vocal tract, see the peaks at about 800 and 1600 Hz but that there is an absence of sharp frequency components in the spectrum. These intuitive differences are captured in a cepstral coefficient representation and a neural network can be trained to differentiate the various types of audio events.

A cough-detection algorithm may count the number and severity of coughing events over the course of a day. The number and severity of coughs within a rolling window of time, such as a 15-minute period, could be tracked and compared to a threshold value. One does not have to collect large quantities of raw data and analyze it later to assess the coughing frequency and severity. Real-time data can be filtered to identify impulsive events. For example, as the integrated power spectral densities are computed as defined in Equation 1, large changes in the index from one sample to the next can be searched and identified. A one second interval containing a cough would display a large jump in this index. These events could be time-stamped and stored.

In some embodiments, the device can directly monitor the chosen parameters employing electronic circuits that measure the signal power at user-selected frequencies. Such circuits, which operate on the raw input signal in its analog (continuous) form, do not rely on conversion of the signal to digital format and digital computing circuits. Such analog signal processing circuits (technically known as switched capacitor filter banks) operate with far lower power than their digital counterparts. A similar technology has been employed in cochlear implants which rely on extreme miniaturization and low power consumption.

Measurement of a patient's wheezing and coughing while they are sleeping is particularly useful in several aspects. First, it provides a baseline measurement when the patient is known to be at a low level of activity. Second, the background noise is typically reduced, increasing the amount of 'good' data obtained. In addition, the occurrence of wheezing and coughing during sleep is typically not reported in self-assessment of a patient's condition and may be the most indicative data on a patient's underlying condition.

The correlation of measured parameters with a value related to the severity of symptoms is based on studies done with large populations of individuals and the results of standard spirometry tests as well as user surveys, daily symptom diaries, or health care utilization. While this provides an average value for use in determining severity, there can be variation in the response among individuals which produces variance in the desired correlation. Use of this average correlation provides a base level of valuable data to the patient and their doctor. Providing the device with the capability of learning the particular capabilities of the individual using the device allows improved accuracy it determining whether a given condition of wheezing and coughing is serious or simply represents this individual's response to a given level of activity. The ability to establish a personal baseline and to adjust threshold values in relation to this baseline provides a higher level of benefit and reduces the likelihood of false alarms which may result in user frustration and discontinuation of use of the device.

One approach to training the device for the particular characteristics of an individual is to have the patient wear the device while performing a prescribed set of exercises such as a defined rate of walking on a treadmill or climbing steps at a prescribed rate. This could be done under the supervision of the patient's doctor and allow the doctor to adjust parameters based on the patient's performance and the measured responses.

Another approach may involve reading a specific block of text much as done with normal speech-to-text recognition programs to train the device to accommodate variation in the pitch and frequency of individual patients. Speech detection algorithms, in particular, may require some training to properly recognize when the individual is speaking and discriminate between speech and the desired "symptoms of interest."

This device measures and analyzes at least three separate characteristics of the patient's behavior and symptoms—wheezing, coughing, and level of activity. In addition to storing the data, the device can also be capable of providing user feedback via a graphical display as well as an alarm to the user when symptom severity reaches a preset level so that patients can take appropriate management actions. The display can also provide information to the user such as the frequency and duration of asthma symptoms, both wheeze and cough, and it can provide historical summaries of symptoms to enable users and clinicians to monitor long-term trends of symptoms. This is where the activity monitoring function is an important feature. If the asthma symptoms are severe for a low level of physical activity, a potentially serious condition could be indicated; whereas if symptoms resulted from strenuous physical exercise, the condition could be less serious.

Another feature is use of longitudinal data to establish normal levels for each individual and to provide user alerts when current measured symptoms exceed the user's norm. For example, the duration of wheezing symptoms following a period of exertion can be used as an indicator of the severity of asthma. Faster recovery time indicates lesser severity. Over time, the system can learn the response of the individual user and if the system detects an increase in the recovery time, the user can be alerted to a worsening of their condition. Learning the individual in this way can be applied to a number of attributes of wheezing and coughing combined with the acceleration measurements. An example of this is to track the severity of coughing symptoms following exercise. Conversely, the level of user activity following a period of wheezing or coughing could indicate user response and compensation to symptoms, a marked decrease in activity could indicate compensation for severe symptoms.

In addition to the detection and measurement of wheezing and cough which occur during exhalation, it is also possible to monitor the breathing during inhalation with the same equipment. One valuable objective in analyzing a patient's breathing during inhalation is to detect "stridor." Stridor is an abnormal, high-pitched, musical breathing sound caused by a blockage in the throat or voice box (larynx). Children are at higher risk of airway blockage because they have narrower airways than adults. In young children, stridor is a sign of airway blockage and should be treated right away to prevent total airway obstruction. Children who are already at risk with asthma may be more likely to be affected by an airway blockage due to diseases such diphtheria or pneumococchus or simply due to inadvertently swallowing an object such as a peanut and having it lodge in their throat. Using the same time-analysis and frequency-analysis techniques as used to detect wheezing and cough, this device can detect the sounds characteristic of stridor and send an alarm message if a threshold value is reached.

A further feature of the device may include a button or other actuator that allows the user to indicate that they have just self-administered a dose of asthma medication. This would provide a time-stamped event that could be correlated with subsequent changes in wheezing, couching, or activity to provide greater insight to the doctor and patient as to the effectiveness of the medication and feedback on their behavior. This would also avoid incorrect conclusions based on changes in wheezing or coughing or activity levels and the source of the change.

Some methods of monitoring a respiratory illness include detecting a patient sound, comprising at least one of an abnormal breath sound of a patient and a cough sound of the patient; detecting a movement of at least part of the patient; determining a correlation between an indicator of the patient sound and an indicator of the movement; outputting to an output device an indicator, based on the correlation, of at least one of a severity of the respiratory illness and a probability of a respiratory illness-related event of the patient. Some methods provide that the respiratory illness comprises asthma. Some methods provide that the abnormal breath sound comprises at least one of a wheeze, a rhonchus, a diminished breath sound, and stridor. Some methods provide that the indicator of the movement comprises an acceleration.

Some embodiments provide a system for monitoring asthma that includes a sound detector that detects a patient sound, comprising at least one of an abnormal breath sound of a patient and a cough of the patient; a movement detector that detects a movement of at least part of the patient; a processor that determines a correlation between an indicator of the patient sound and an indicator of the movement; an output device that outputs, based on the correlation, an indicator of at least one of a severity of asthma and a probability of an asthma-related event of the patient.

Some embodiments describe an asthma monitoring system that includes a vibration sensing device, configured to detect a vibration over at least a portion of an audible spectrum and to output data indicative of detected vibration; an acceleration sensing device, configured to detect acceleration and to output data indicative of detected acceleration; and a processor configured to receive the data indicative of detected vibration and the data indicative of detected acceleration; wherein the processor processes the data indicative of detected vibration and the data indicative of detected acceleration, and the processor outputs a report based on an association between (a) at least a portion of the data indicative of detected vibration, corresponding to at least one asthma-related symptom, and (b) at least a portion of the data indicative of detected acceleration.

Some embodiments describe an asthma monitoring system that includes a sound sensing device that detects sound over at least a portion of the audible spectrum and converts the detected sound to a sound signal; an acceleration sensing device that detects acceleration and converts the detected acceleration to an acceleration signals; an output device; and a computation module, operably connected to the sound sensing device, the acceleration sensing device, and the output device, the computation module comprising: a memory, containing instructions for processing the sound signal and the acceleration signal; a communication module configured to transmit signals to an external device; and a processor module, operably connected to the memory, the communication module, and the output device, and configured to receive the sound signal and the acceleration signal; wherein the processor module retrieves the instructions from the memory, processes the sound signal and the acceleration signal according to the instructions, stores data generated according to the instructions, sends at least one signal generated according to the instructions to the output device, and sends data through the communication module to the external device according to the instructions.

Some embodiments of the system provide that the output devices comprises an audio device. Some embodiments of the system provide that the instructions comprise at least one algorithm that converts a time waveform of the sound signal into a frequency representation and performs time-domain analysis and frequency-domain analysis of at least one of the sound signal and the acceleration signal. Some embodiments of the system provide that the instructions further comprise at least one algorithm capable of discriminating an asthma symptom from another sonic event in the sound signal. Some embodiments of the system provide that the instructions further comprise an algorithm that measures peaks of the frequency representation at frequencies in about the 200-800 Hz range, and compares these to a predetermined value associated with wheezing that is stored in the memory. Some embodiments of the system provide that the instructions further comprise an algorithm that measures an amplitude and duration of a sonic event of the sound signal and measures a power spectral density over a selected band of frequencies, and compares the power spectral density to a predetermined value associated with coughing that is stored in the memory. Some embodiments of the system provide that the instructions further comprise an algorithm that measures a spectral centroid of the sound signal. Some embodiments of the system provide that the instructions further comprise an algorithm that measures a spectral-peak-to-noise ratio of the sound signal.

Some embodiments of the system provide that the instructions further comprise an algorithm that measures a time characteristic and a spectral characteristic of the acceleration signal and compares these measurements to predetermined values associated with at least one level of activity stored in the memory. Some embodiments of the system provide that the instructions further comprise an algorithm that detects a sonic event in a time waveform of the sound signal, discriminates an asthma symptom from another sonic event, measures an amplitude and a duration of the symptom, measures a power spectral density over a selected band of frequencies, and compares the amplitude and the duration and the power spectral density of the symptom to predetermined values associated with coughing that are stored in the memory, measures a peak of a frequency representation of the symptom at frequencies in about the 200-800 Hz range, and compares the measured peak to a predetermined value associated with wheezing that is stored in the memory, and uses a combination of the cough comparison, the wheezing comparison, and the activity level to produce an indication of at least one of an asthma severity and a likelihood of worsening of an asthma condition.

Some embodiments of the system provide that the computation module further comprises a circuit that measures power of the sound signal and of the acceleration signal at selected frequencies and passes the power measurements to the processor module. Some embodiments of the system further comprise a visual output device that is operably connected to the processor, wherein the processor sends at least one visual signal to the visual output device when appropriate according to the instructions. Some embodiments of the system provide that the visual output device displays at least one of text and a graphic image.

Some embodiments of the system provide that the sound sensing device comprises a microphone. Some embodiments of the system provide that the output device comprises an audio speaker. Some embodiments of the system provide that the acceleration sensing device measures acceleration in more than one non-parallel axis and produces signals representing accelerations in three orthogonal axes.

Some embodiments of the system provide that the computation module is contained in at least one of a cell phone, a personal digital assistant (PDA), a handheld computer, a pager, and a portable media player. Some embodiments of the system provide that the acceleration sensing device communicates wirelessly with the computation module. Some embodiments of the system provide that the acceleration sensing device is contained in the same cell phone, personal digital assistant (PDA), handheld computer, pager, or portable media player. Some embodiments of the system provide that the audio output device comprises a speaker and the sound sensing device comprises a microphone, and the speaker and the microphone communicate wirelessly with the computation module. Some embodiments of the system provide that the sound sensing device comprises a microphone, and the microphone and the acceleration sensing device communicate wirelessly with the computation module.

Some embodiments of the system provide that the vibration sensing device, the acceleration sensing device, and the processor are contained in a single device. Some embodiments of the system further comprises the external device.

Some embodiments describe a method of monitoring asthma of a patient, comprising: generating a sound signal, from detected sound in at least a portion of an audible spectrum; generating an acceleration signal, from detected acceleration of at least part of the patient's body; determining a correlation between the sound signal and the acceleration signal, according to program instructions stored in a computer-readable memory; sending an indicator signal to an output device when the correlation is indicative of at least one of (a) exceeding a threshold value of a severity of asthma, and (b) exceeding a threshold value of a probability of an asthma-related event, wherein the indicator signal results in the output device indicating at least one of the severity of asthma and the probability.

Some methods provide that the detected sound comprises at least one of a sound of a cough and an abnormal breath sound of the patient. Some methods provide that the abnormal breath sound comprises at least one of a wheeze, a rhonchus, a diminished breath sound, and stridor.

The disclosure has been described with reference to specific embodiments thereof. It will, however, be evident that various modifications and changes may be made thereto without departing from the broader spirit and scope of the disclosure. The specification and drawings are, accordingly, to be regarded in an illustrative rather than a restrictive sense.

What is claimed is:

1. An asthma monitoring system, comprising:
a sound sensing device that detects sound over at least a portion of the audible spectrum and converts the detected sound to a sound signal;
an acceleration sensing device that detects acceleration and converts the detected acceleration to an acceleration signal;
an output device; and
a computation module, operably connected to the sound sensing device, the acceleration sensing device, and the output device, the computation module comprising:
a memory, containing instructions for processing the sound signal and the acceleration signal, wherein the instructions comprise at least one algorithm that converts a time waveform of the sound signal into a frequency representation and performs time-domain analysis and frequency-domain analysis of at least one of the sound signal and the acceleration signal, and wherein the instructions further comprise an algorithm that measures a spectral-peak-to-noise ratio of the sound signal;

a communication module configured to transmit signals to an external device; and a processor module, operably connected to the memory, the communication module, and the output device, and configured to receive the sound signal and the acceleration signal;

wherein the processor module retrieves the instructions from the memory, processes the sound signal and the acceleration signal according to the instructions, stores data generated according to the instructions, sends at least one signal generated according to the instructions to the output device, and sends data through the communication module to the external device according to the instructions; wherein the at least one signal is generated based on the frequency representation, the time-domain analysis, the frequency-domain analysis, and the spectral-peak-to-noise ratio.

2. The system of claim 1, wherein the instructions further comprise at least one algorithm capable of discriminating an asthma symptom from another sonic event in the sound signal; wherein the at least one signal is generated further based on a result of the discriminating.

3. The system of claim 1, wherein the instructions further comprise an algorithm that measures peaks of the frequency representation at frequencies in about the 200-800 Hz range, and compares these to a predetermined value associated with wheezing that is stored in the memory; wherein the at least one signal is generated further based on the peaks of the frequency representation.

4. The system of claim 1, wherein the instructions further comprise an algorithm that measures an amplitude and duration of a sonic event of the sound signal and measures a power spectral density over a selected band of frequencies, and compares the power spectral density to a predetermined value associated with coughing that is stored in the memory; wherein the at least one signal is generated further based on the power spectral density.

5. The system of claim 1, wherein the instructions further comprise an algorithm that measures a spectral centroid of the sound signal; wherein the at least one signal is generated further based on the spectral centroid.

6. The system of claim 1, wherein the instructions further comprise an algorithm that measures a time characteristic and a spectral characteristic of the acceleration signal and compares these measurements to predetermined values associated with at least one level of activity stored in the memory; wherein the at least one signal is generated further based on the time characteristic and the spectral characteristic.

7. The system of claim 6, wherein the instructions further comprise an algorithm that detects a sonic event in a time waveform of the sound signal, discriminates an asthma symptom from another sonic event, measures an amplitude and a duration of the symptom, measures a power spectral density over a selected band of frequencies, and compares the amplitude and the duration and the power spectral density of the symptom to predetermined values associated with coughing that are stored in the memory, measures a peak of a frequency representation of the symptom at frequencies in about the 200-800 Hz range, and compares the measured peak to a predetermined value associated with wheezing that is stored in the memory, and uses a combination of the cough comparison, the wheezing comparison, and an activity level to produce an indication of at least one of an asthma severity and a likelihood of worsening of an asthma condition; wherein the at least one signal is generated further based on the indication and the likelihood.

8. The system of claim 1, wherein the computation module further comprises a circuit that measures power of the sound signal and of the acceleration signal at selected frequencies and passes the power measurements to the processor module.

9. The system of claim 1, wherein the output device comprises an audio speaker.

10. The system of claim 1, wherein the acceleration sensing device measures acceleration in more than one non-parallel axis and produces signals representing accelerations in three orthogonal axes.

11. The system of claim 1, wherein the computation module is contained in at least one of a cell phone, a personal digital assistant (PDA), a handheld computer, a pager, and a portable media player.

12. The system of claim 11, wherein the acceleration sensing device communicates wirelessly with the computation module.

13. The system of claim 11, wherein the acceleration sensing device is contained in the same cell phone, personal digital assistant (PDA), handheld computer, pager, or portable media player.

14. The system of claim 1, further comprising the external device.

15. The system of claim 1, wherein the sound comprises at least one of a sound of a cough and an abnormal breath sound of the patient.

16. The system of claim 1, wherein the sound comprises at least one of a wheeze, a rhonchus, a diminished breath sound, and stridor.

17. The system of claim 1, wherein the sound sensing device is a vibration sensing device.

18. The system of claim 1, wherein the computation module comprises a visual output device.

19. The system of claim 1, wherein the system is configured to download the instructions from the external device.

20. The system of claim 1, wherein the communication module is configured to communication with the external device over a wireless link.

* * * * *